(12) United States Patent
Gough

(10) Patent No.: US 8,764,690 B2
(45) Date of Patent: Jul. 1, 2014

(54) COMPRESSION SYSTEM

(75) Inventor: Nigel Gough, Cardiff (GB)

(73) Assignee: Huntleigh Technology Limited (GB)

( * ) Notice: Subject to any disclaimer, the term of this patent is extended or adjusted under 35 U.S.C. 154(b) by 981 days.

(21) Appl. No.: 12/514,163

(22) PCT Filed: Nov. 6, 2007

(86) PCT No.: PCT/GB2007/004168
§ 371 (c)(1),
(2), (4) Date: May 12, 2009

(87) PCT Pub. No.: WO2008/056108
PCT Pub. Date: May 15, 2008

(65) Prior Publication Data
US 2010/0036299 A1    Feb. 11, 2010

(30) Foreign Application Priority Data
Nov. 10, 2006    (GB) .................................... 0622415.8

(51) Int. Cl.
*A61H 9/00*    (2006.01)
*A61F 13/06*    (2006.01)

(52) U.S. Cl.
USPC ............ 601/152; 601/148; 601/149; 601/151; 602/13; 602/60; 602/62

(58) Field of Classification Search
USPC ........................ 601/148–152; 602/13, 60–63
See application file for complete search history.

(56) References Cited

U.S. PATENT DOCUMENTS

| | | | |
|---|---|---|---|
| 3,177,866 A | 4/1965 | Wesslund | |
| 5,117,812 A * | 6/1992 | McWhorter | 601/149 |
| 5,179,941 A | 1/1993 | Siemssen et al. | |
| 6,080,120 A | 6/2000 | Sandman et al. | |
| 6,123,681 A | 9/2000 | Brown, III | |
| 6,231,532 B1 * | 5/2001 | Watson et al. | 601/150 |
| 2002/0107461 A1 | 8/2002 | Hui | |
| 2004/0054306 A1 * | 3/2004 | Roth et al. | 601/152 |
| 2005/0075531 A1 | 4/2005 | Loeb et al. | |
| 2005/0187503 A1 | 8/2005 | Tordella et al. | |
| 2006/0149176 A1 | 7/2006 | Bolam et al. | |

FOREIGN PATENT DOCUMENTS

| | | |
|---|---|---|
| EP | 0880959 A3 | 12/1998 |
| GB | 2064330 A | 6/1981 |
| WO | WO 2005/082314 A1 | 9/2005 |

* cited by examiner

*Primary Examiner* — Patricia Bianco
*Assistant Examiner* — Keri J Nelson
(74) *Attorney, Agent, or Firm* — Craig A. Fieschko, Esq.; DeWitt Ross & Stevens S.C.

(57) ABSTRACT

The apparatus comprises an inflatable sleeve 6 to be wrapped around a limb, typically a thigh, of a patient. The sleeve 6 comprises three inflatable chambers 3, 4, 5. Inflation is controlled by a pump 1 so that the distal chamber 3 is inflated first to a low pressure to act as a tourniquet, followed by inflation of the central chamber 4 to a pressure to drive fluid flow upwards, and then inflation of the proximal chamber 5 to a low pressure to act as a tourniquet and deflating both the distal 3 and central 4 chambers to produce a negative pressure gradient down-stream in the limb causing fluid to be drawn up the limb. This cycle is repeated a number of times over a period of two minutes before allowing the limb to rest for two minutes, resulting in increased mean arterial blood flow.

20 Claims, 9 Drawing Sheets

0 mmHg 0 mmHg 0 mmHg

COMPRESSION SYSTEM

FIELD OF THE INVENTION

The present invention relates to a compression apparatus and method to apply compression to a limb of a patient.

BACKGROUND OF THE INVENTION

In order for tissues to remain healthy, blood flow and lymph flow have to be optimal. In the healthy organism, optimal flow of these fluids is controlled by the interaction of many homeostatic systems. Prolonged interruption of optimal flow in any of the fluid transport vessels results in tissue deterioration. The drainage flow is as crucial as the supply flow for tissue health. In vascular disease, appropriately augmented blood flow to and from the affected tissues will improve the health of the tissue and promote rapid healing where tissue damage has been sustained.

Prior to the present invention, various compression devices have been known in the art for applying compressive pressure to a patient's limbs in order to improve blood flow. For example, it is known to use intermittent pneumatic compression systems for Deep Vein Thrombosis (DVT) prophylaxis applied to the lower limb both before and after surgery. These systems are used to promote continuous flow within the leg veins preventing blood stasis and subsequent thrombosis. More complex compression systems using a multi-chamber inflatable garment covering the whole limb are available for the treatment of lymphoedema. The chambers are inflated and deflated in a sequential manner to force the excess interstitial fluid in an upward direction. Intermittent compression is also used to promote healing of obstinate venous wounds. All these techniques are applied with a variety of compression cycle times and pressures. However, each technique is only applied to a specific target vessel with little regard to the effects on other vessels, for example, DVT prophylaxis targets the deep veins but the effect on arterial flow is not considered; lymphoedema treatment assumes the promotion of lymphatic flow but the effects on venous and arterial flow are not considered; and veins with incompetent valves are never specifically considered.

SUMMARY OF THE INVENTION

The invention seeks to make improvements.

Accordingly, the present invention provides an apparatus for applying compression to the limb of a patient, the apparatus comprising an inflatable sleeve to be wrapped around a limb, the inflatable sleeve having at least three inflatable chambers, a distal chamber, a central chamber, and a proximal chamber, means for separately inflating the chambers and control means for inflating the chambers in a predetermined sequence and each at a predetermined pressure such that the such that the distal chamber is inflated first to a pressure to occlude the veins but not the arteries in the limb, the centre chamber is inflated next to a pressure to drive the fluid in the limb upwards and lastly the proximal chamber is inflated to a pressure to occlude the veins but not the arteries in the limb and the distal and centre chambers are deflated to promote fluid to be drawn up the limb by creating a negative pressure gradient downstream in the limb. The unique sequence of inflation and deflation of the chambers enables the apparatus to act like a pump incorporating a back flow prevention valve. In this way, the apparatus provides an external venous valve function to compensate for the absence of competent venous valves. Advantageously, for wound healing applications, the apparatus can be applied to the proximal part of the limb away from the wound site providing painless therapy, allowing access to wound dressings and not disturbing the granulating wound bed.

The combination of being able to apply the compression apparatus remote to a distal wound and the unique timing sequence with the low pressure pumping establish almost normal pressure gradients across the distal nutritional capillary beds with no discomfort to the patient.

In the preferred embodiment, the inflation and deflation sequence of the chambers is repeated a plurality of times over a period of two minutes followed by a period of two minutes without any compression. Preferably, the chambers' inflation and deflation sequence is repeated at least six times over the two minute period.

According to a further aspect of the invention there is provided a method of applying compression to the limb of a patient, the method comprising the steps of:

a. locating an inflatable sleeve comprising a distal, central and proximal chamber, on a limb,
b. first, inflating the distal chamber of the sleeve to a low pressure to act as a tourniquet,
c. next, inflating the central chamber of the sleeve to a pressure to drive fluid upwards of the limb,
d. lastly, inflating the proximal chamber of the sleeve to a pressure to act as a tourniquet,
e. and deflating both the central and distal chambers to produce a negative pressure gradient downstream in the limb to promote fluid flow to be drawn up the limb.

Preferably the steps are repeated several times, and more preferably six times, over a period of two minutes followed by a period of rest for two minutes

BRIEF DESCRIPTION OF THE DRAWINGS

The invention will now be described in detail, by way of example only with reference to the following drawings, in which.

DETAILED DESCRIPTION OF PREFERRED VERSIONS OF THE INVENTION

Figure 1:
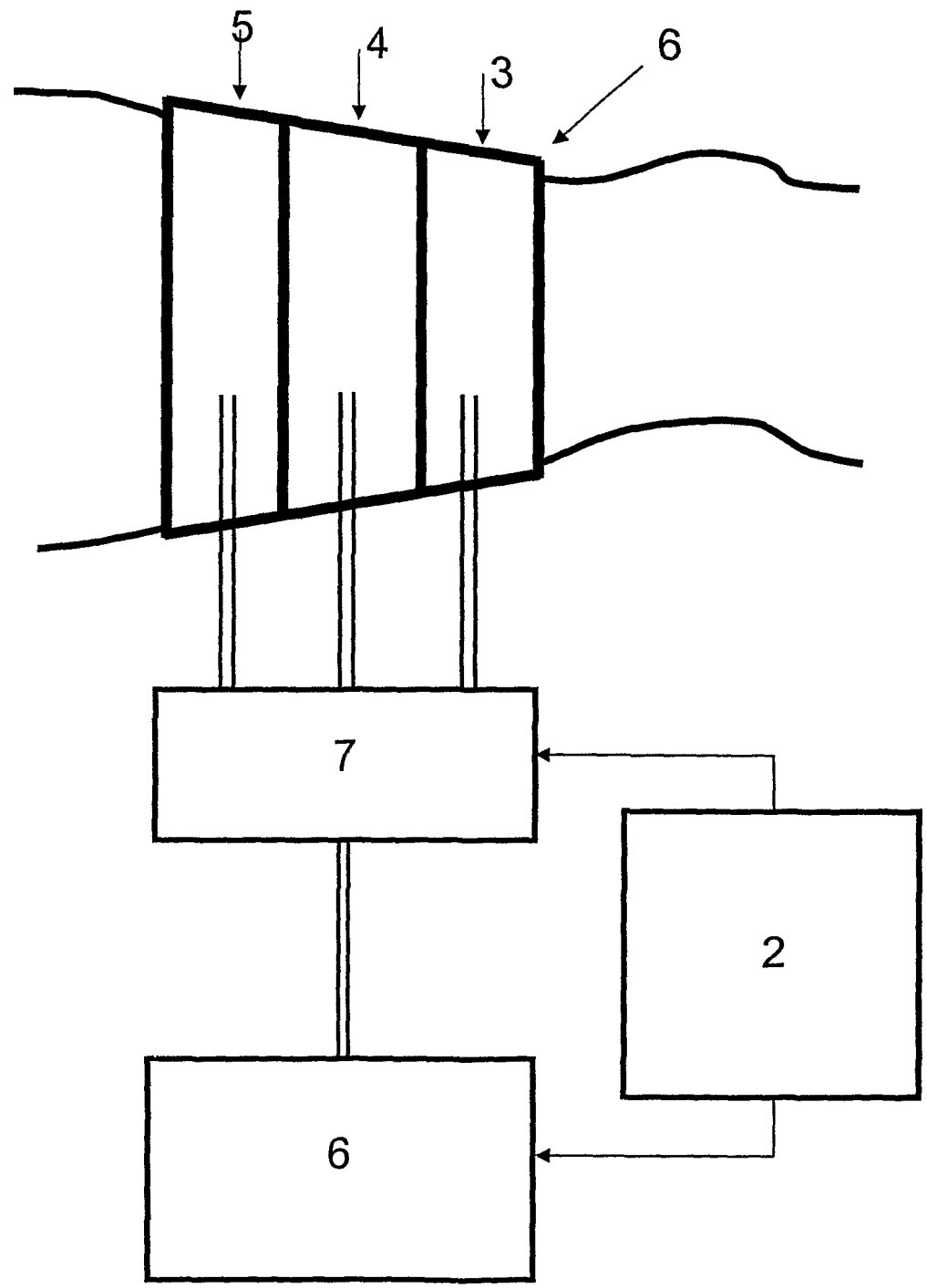
FIG. 1 is a schematic view of the compression apparatus according to the invention.
Figure 2A:
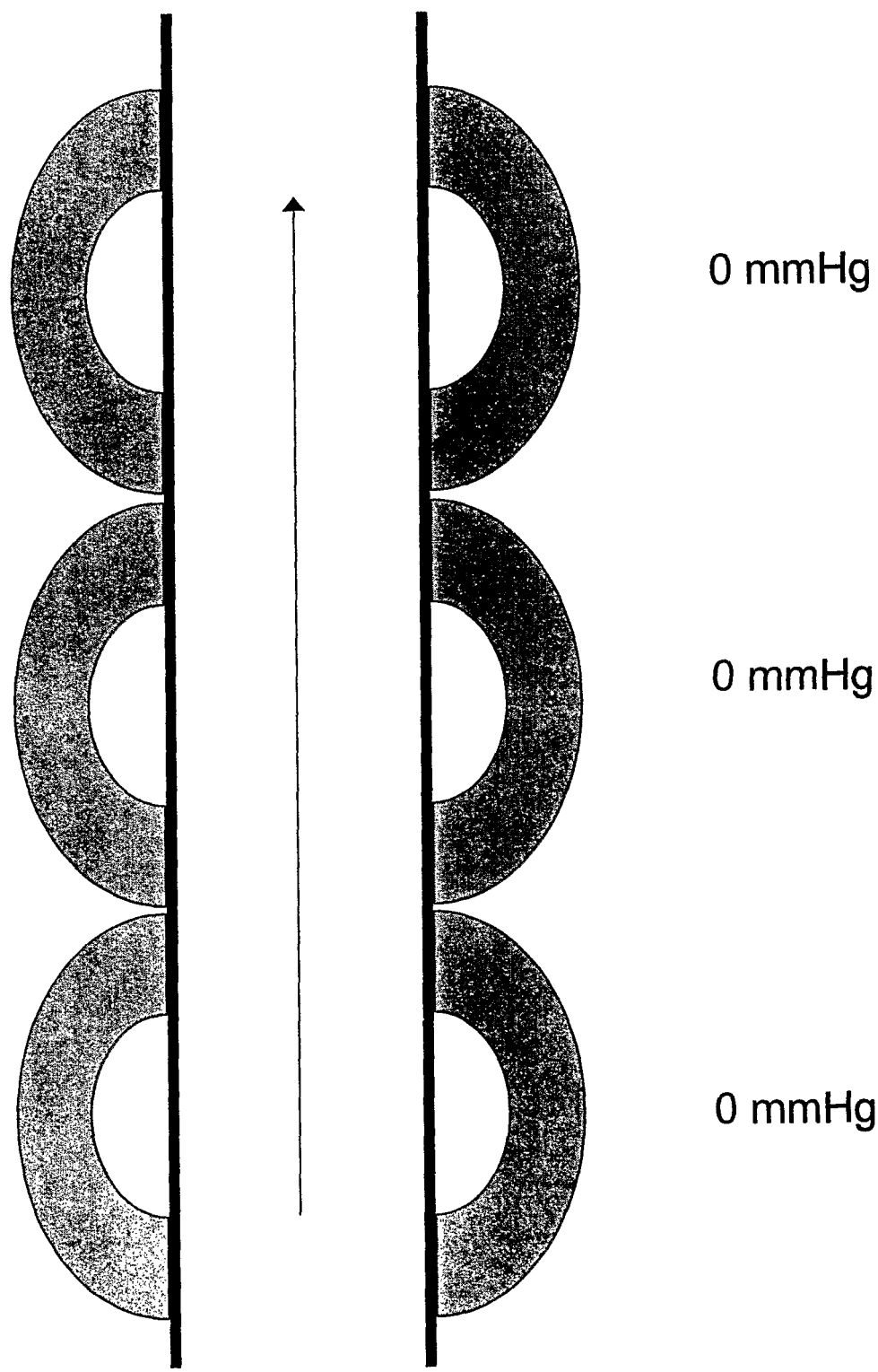
FIGS. 2a, 2b, 2c, 2d and 2e show the sequence of compression of the chambers in the garment in FIG. 1 according to the invention.
Figure 2B:
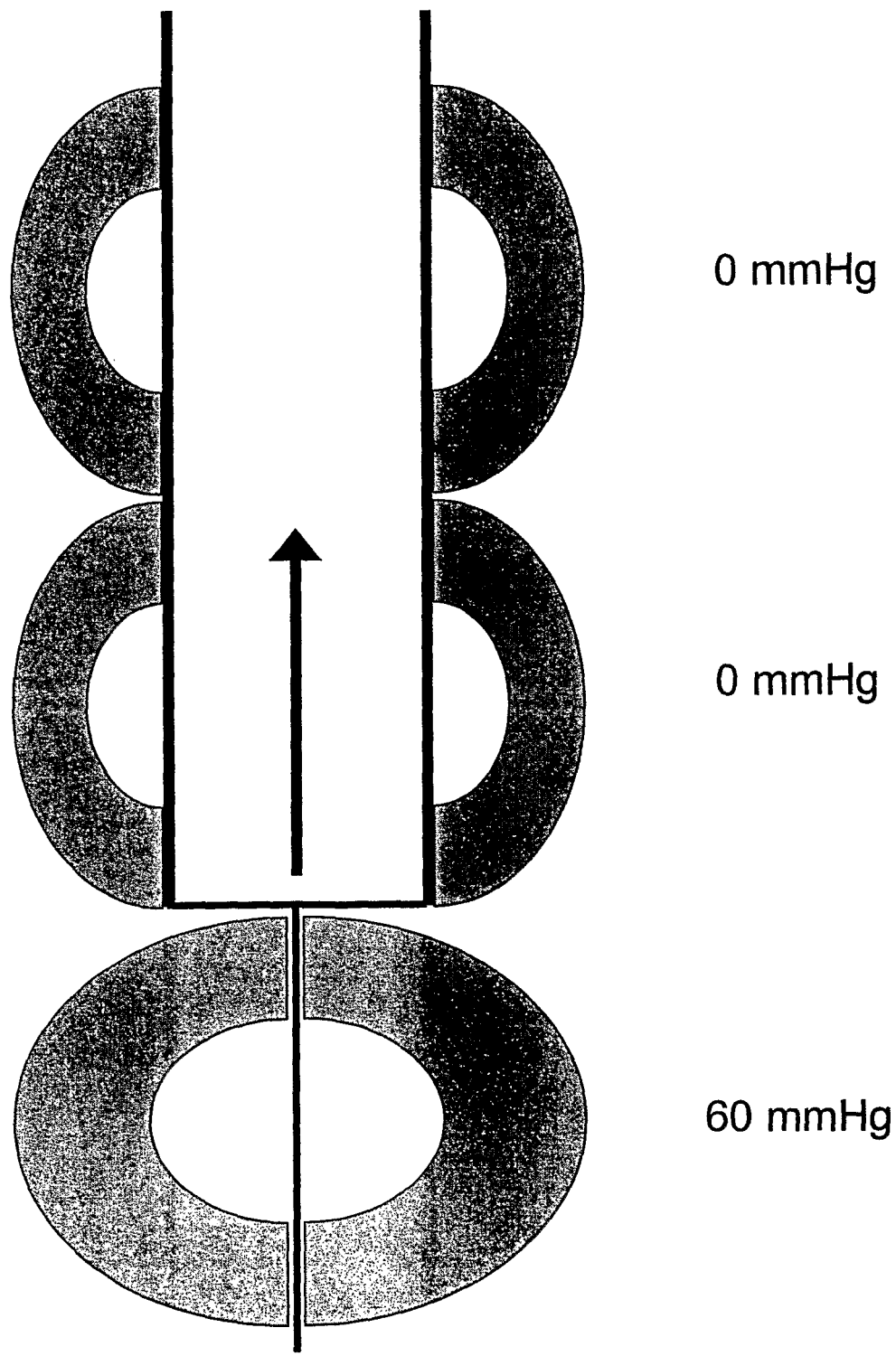
Figure 2C:
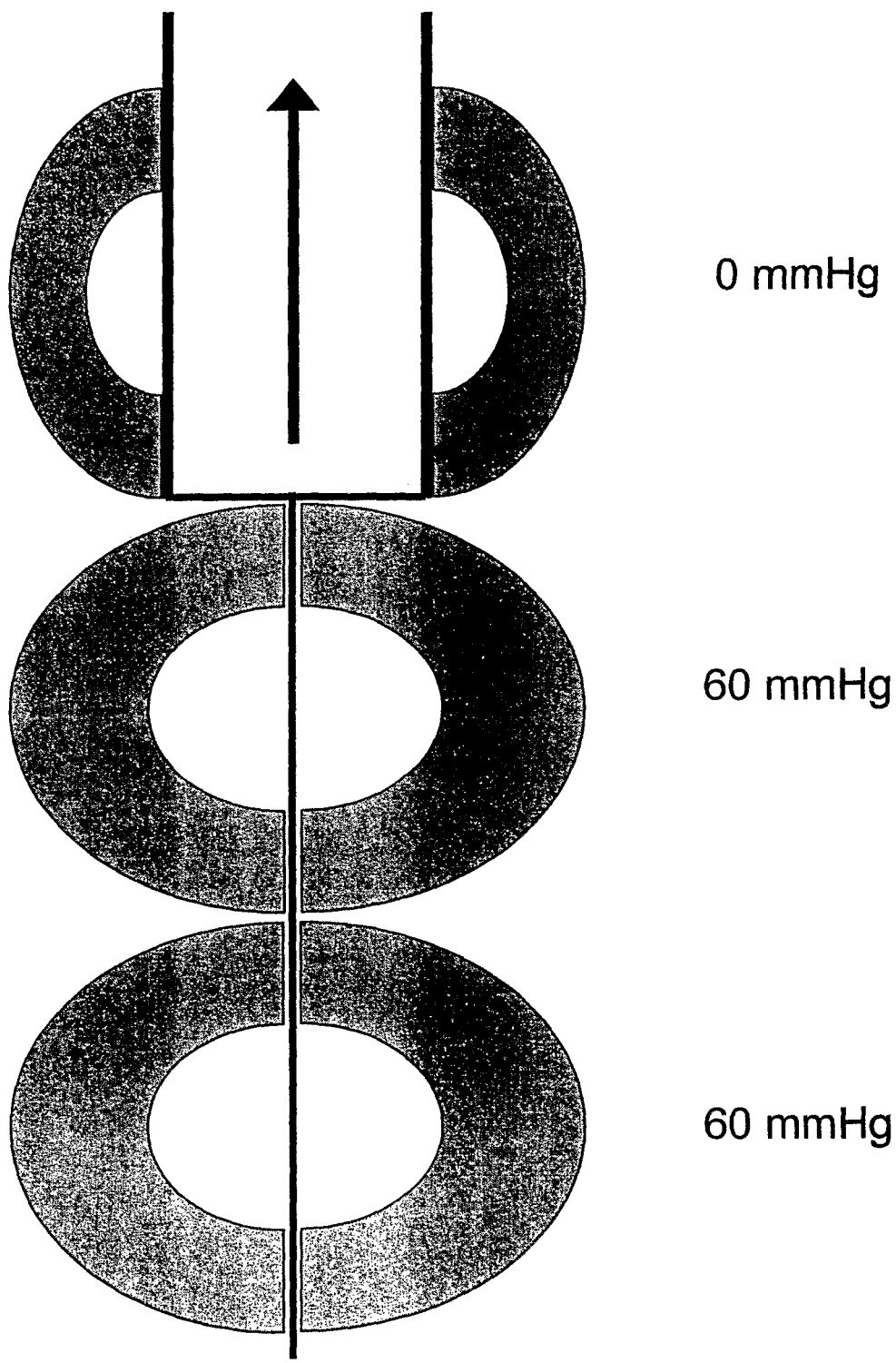
Figure 2D:
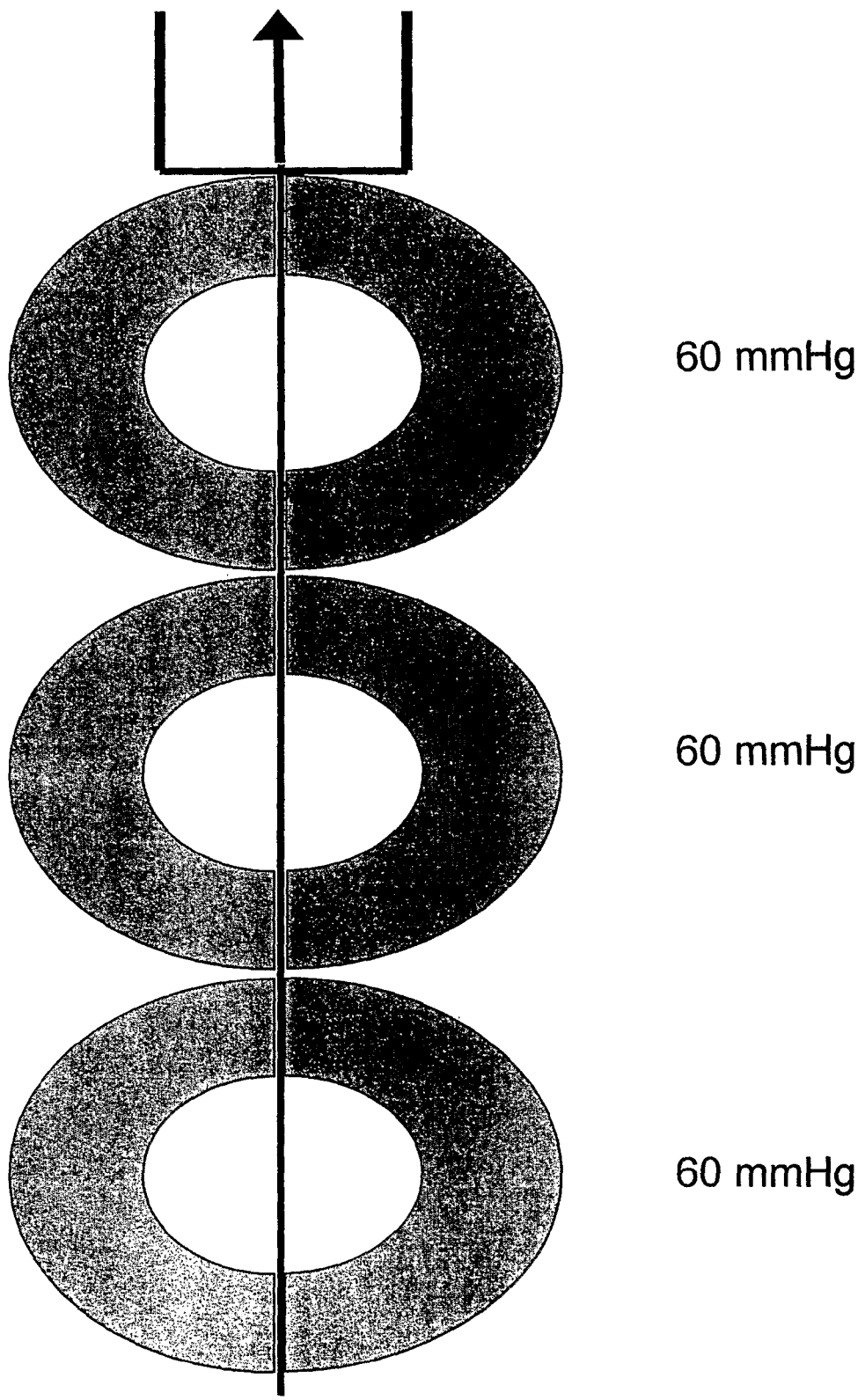
Figure 2E:
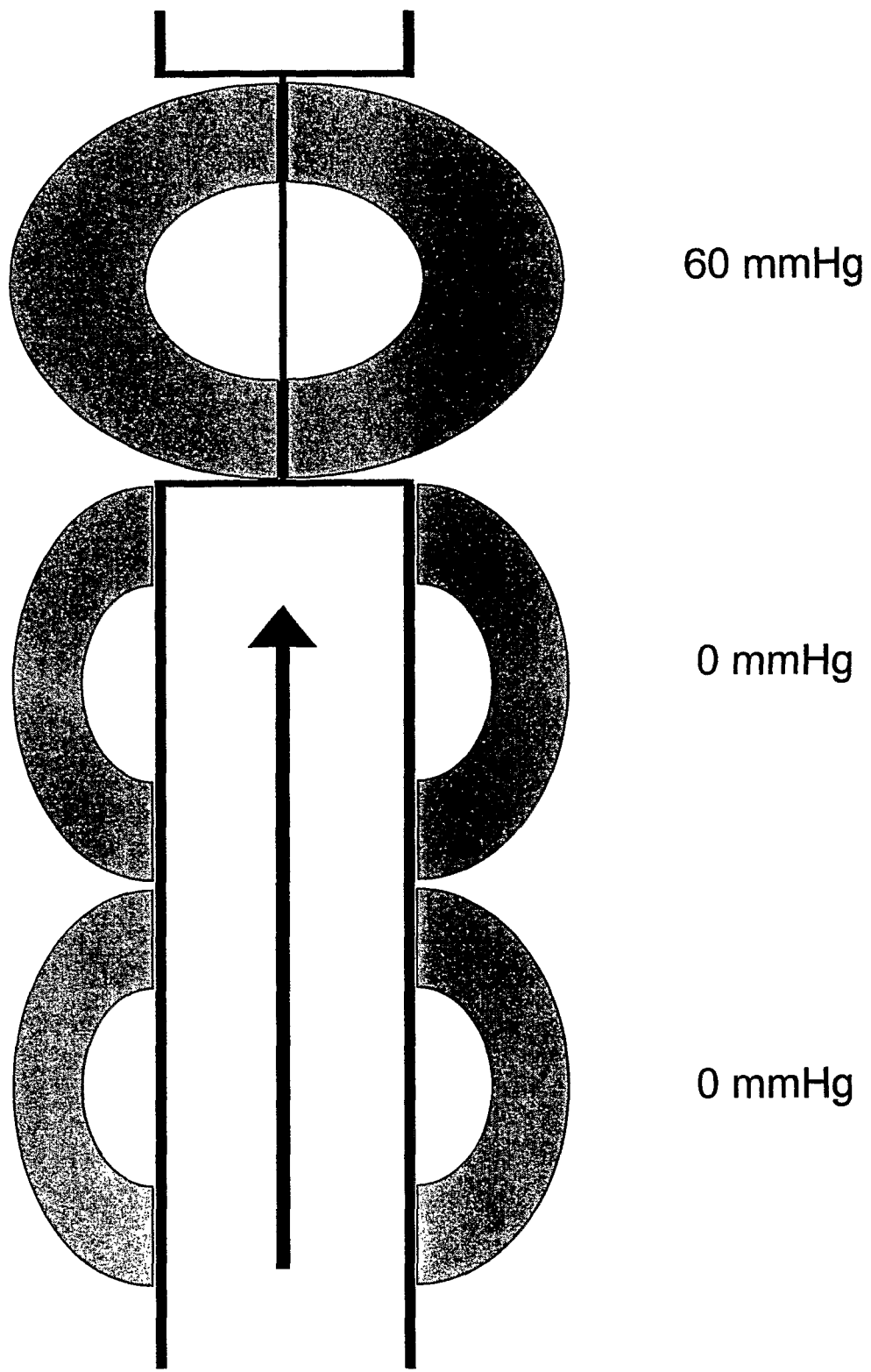
Figure 3:
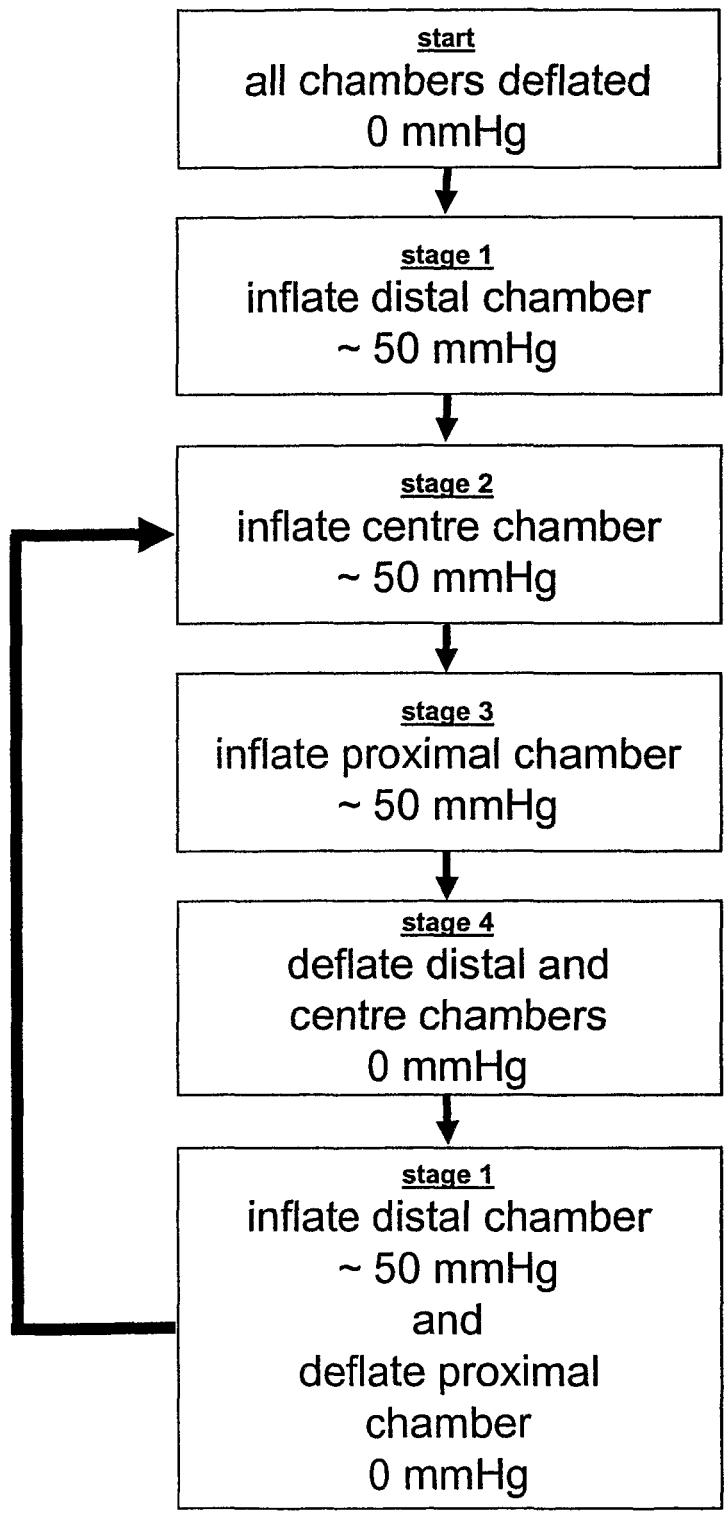
FIG. 3 shows a flow diagram of the chamber inflation/deflation sequence shown in FIGS. 2a to e.

Referring to FIG. 1, the compression system according to the present invention is typically applied to the thigh of a leg but can be applied to other areas of the leg and other limbs. The pump 1 is connected to the garment 6 and each of the chambers, the distal chamber 3, the central chamber 4 and the proximal chamber 5. The garment 6 can be constructed in a variety of ways including wrap around and secured with hook and pile fastenings or similar. The pump 1, consisting of a compressor 6, a valve block 7 and valve timing and pressure regulation control means 2, is controlled to sequentially inflate and deflate the chambers 3, 4, 5 in a predetermined sequence and at predetermined pressures to provide a pump action to the veins and lymphatics and also apply a simultaneous hyperaemic stimulus to the arteries. For veins with incompetent valves, the three chamber arrangement acts as an external venous valve function. Using applied pressures of approximately diastolic blood pressure, uninterrupted physiological fluid flow is promoted simultaneously in all of the three fluid conduits, namely the veins, arteries and lymphatics.

In use, when applied on a thigh the distal and proximal chambers 3 and 5 are inflated to a pressure so as to behave as low pressure tourniquets that will occlude the veins but not the arteries. The central chamber 4 compresses a substantial portion of a vein so as to force blood upward towards the pelvis while the distal chamber 3 is compressed. The sequence as shown in FIGS. 2a to 2e and FIG. 3, comprises the following steps:— i. Inflate distal chamber 3 to prevent back pressure from central chamber 4 when inflated (particularly in the presence of incompetent venous valves).
ii. Inflate central chamber 4 to drive blood in vein towards the pelvis.
iii. Inflate proximal chamber 5 to support proximal blood column.
iv. Deflate distal 3 and centre 4 chambers, producing a negative pressure gradient from the feet causing blood to be drawn up the leg.
v. Repeat the cycle.

The pressures and cycle times can be adjusted to account for specific needs and conditions.

Figure 4:
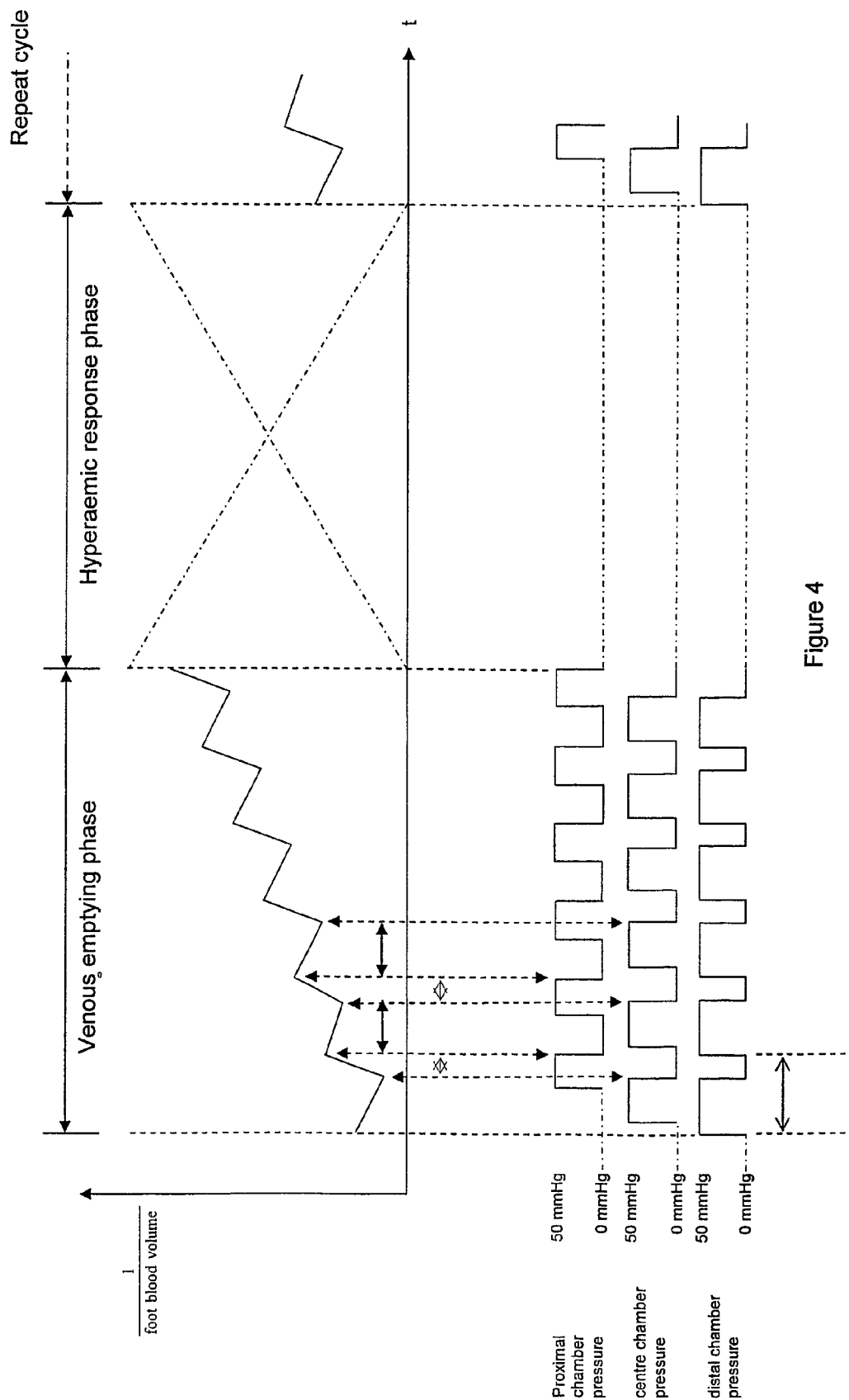
FIG. 4 shows the pressure time profiles of the chambers in the garment according to a preferred embodiment of the invention.

FIG. 4 shows the compression sequence of a preferred embodiment of the invention where the compression apparatus has an inflation and deflation regime comprising an overall cycle of four minutes, the first two minutes consisting of six twenty second venous pump cycles followed by two minutes of no compression to allow the full effect of the elevated arterial inflow due to the stimulated hyperaemic response. The low venous pressure compression at the thigh also augments venous and lymphatic outflow from the distal tissue during the first 2 minutes.

Figure 5:
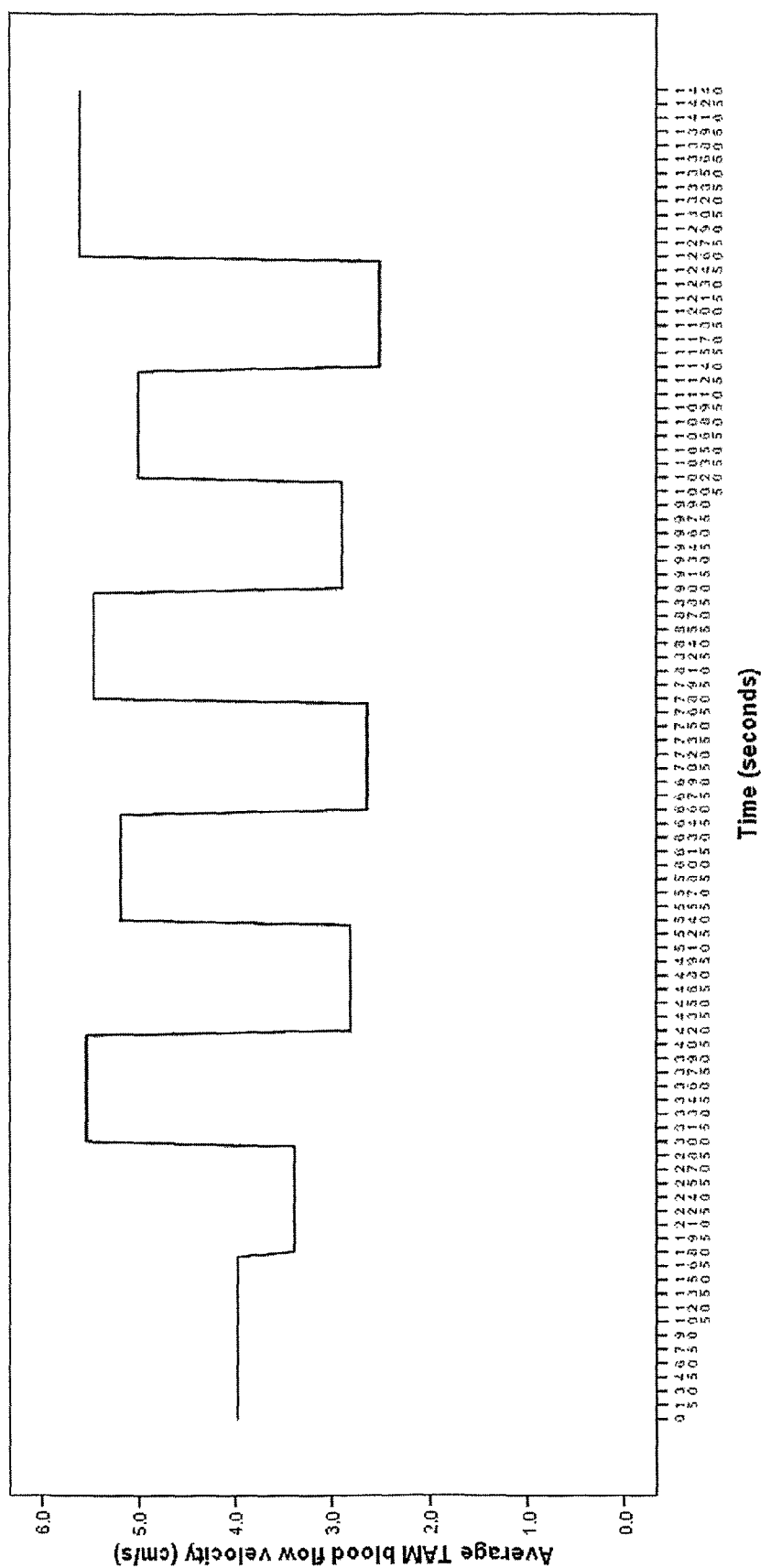
FIG. 5 shows the arterial inflow hyperaemic response for the inflation/deflation cycle according to a preferred embodiment of the invention.

FIG. 5 shows the hyperaemic response resulting from applying the compression garment according to a preferred embodiment of the invention as shown in FIG. 4, by the increased time averaged mean arterial blood flow during the two minute cessation of the compression cycle.

These effects combine to restore tissue perfusion to almost normal. This is supported by tests which show that using the compression system of the invention, distal blood volume decreased and venous blood velocity increased particularly in the superficial veins. The compression apparatus has been seen to simulate the venous valve action particularly important for venous insufficiency.

The invention claimed is:

1. A method for applying compression to the limb of a patient using a sleeve having:
   (1) an internal sleeve passage having a length along which a limb may be situated, and
   (2) chambers arrayed along the length of the sleeve passage, the chambers including at least:
      (a) a distal chamber,
      (b) a proximal chamber, and
      (c) a central chamber therebetween,
   the method including the ordered inflation/deflation steps of:
   a. inflating the distal chamber to a distal chamber inflation pressure while the proximal chamber is deflating or in a deflated state;
   b. inflating the central chamber to a central chamber inflation pressure while the distal chamber remains inflated to at least the distal chamber inflation pressure;
   c. inflating the proximal chamber to a proximal chamber inflation pressure while:
      (1) the central chamber remains inflated to at least the central chamber inflation pressure, and
      (2) the distal chamber remains inflated to at least the distal chamber inflation pressure; and
   d. deflating the inflated distal and central chambers while the proximal chamber remains inflated to at least the proximal chamber inflation pressure.

2. The method of claim 1 wherein the ordered inflation/deflation steps are repeated.

3. The method of claim 2 wherein the ordered inflation/deflation steps are repeated at least six times over a period of two minutes, wherein there is always at least one inflated chamber throughout the period.

4. The method of claim 2 wherein:
   a. after several repetitions of the ordered inflation/deflation steps, the chambers are deflating or left deflated for a period of two to four minutes; and
   b. the ordered inflation/deflation steps are thereafter repeated.

5. The method of claim 1 wherein:
   a. the ordered inflation/deflation steps are repeated several times over a first period;
   b. the chambers are left deflating or in a deflated state over a subsequent second period, wherein the second period is at least substantially the same as the first period.

6. The method of claim 5 wherein the first period is about two minutes.

7. The method of claim 6 wherein during the first period, the ordered inflation/deflation steps are repeated at least six times, wherein at all times throughout the first period, at least one chamber is inflated.

8. The method of claim 1 further including the step of fitting a patient's limb within the sleeve passage, the patient's limb terminating in an extremity, wherein the extremity is situated closer to the distal chamber than to the proximal chamber.

9. The method of claim 1 wherein the sleeve passage has a diameter which is:
   a. greater adjacent the proximal chamber, and
   b. lesser adjacent the distal chamber.

10. A device for applying compression to the limb of a patient, the device including:
    a. a sleeve having:
       (1) an internal sleeve passage having a length along which a limb may be situated, and
       (2) chambers arrayed along the length of the sleeve passage, the chambers including at least:
          (a) a distal chamber,
          (b) a proximal chamber, and
          (c) a central chamber therebetween,
    b. a control configured to perform the following inflation/deflation steps in order:
       (1) inflating the distal chamber to a distal chamber inflation pressure while the proximal chamber is deflating or in a deflated state;
       (2) inflating the central chamber to a central chamber inflation pressure while the distal chamber remains inflated to at least the distal chamber inflation pressure;
       (3) inflating the proximal chamber to a proximal chamber inflation pressure while:

(a) the central chamber remains inflated to at least the central chamber inflation pressure, and
(b) the distal chamber remains inflated to at least the distal chamber inflation pressure; and (4) deflating the inflated distal and central chambers while the proximal chamber remains inflated to at least the proximal chamber inflation pressure.

11. The device of claim 10 wherein the sleeve passage has a diameter which is:
   a. greater adjacent the proximal chamber, and
   b. lesser adjacent the distal chamber.

12. The device of claim 10 wherein the control repeats the inflation/deflation steps several times over a period of around two minutes without pausing between the repeated inflation/deflation steps, followed by a period of around two minutes of rest.

13. The device of claim 10 wherein the control repeats the inflation/deflation steps at least six times over a period of about two minutes, without having all chambers deflated at the same time during the period.

14. The device of claim 10 wherein the internal sleeve passage has a diameter of at least about 50 cm, whereby the sleeve may be fit about a patient's thigh.

15. A method for applying compression to the limb of a patient including the steps of:
   a. fitting a sleeve about the patient's limb, the sleeve having:
      (1) a distal chamber located closer to the limb's extremity,
      (2) a proximal chamber located closer to where the limb extends from the body, and
      (3) a central chamber therebetween;
   b. subsequently repeating the following inflation/deflation steps in order:
      (1) inflating the distal chamber to a distal chamber inflation pressure while the proximal chamber is deflating or in a deflated state;
      (2) inflating the central chamber to a central chamber inflation pressure while the distal chamber remains inflated to at least the distal chamber inflation pressure;
      (3) inflating the proximal chamber to a proximal chamber inflation pressure while:
         (a) the central chamber remains inflated to at least the central chamber inflation pressure, and
         (b) the distal chamber remains inflated to at least the distal chamber inflation pressure; and
      (4) deflating the inflated distal and central chambers while the proximal chamber remains inflated to at least the proximal chamber inflation pressure.

16. The method of claim 15 wherein the ordered inflation/deflation steps are performed at least six times over a two minute period without pausing between the repeated inflation/deflation steps, such that throughout the period, at least one of the chambers is inflated.

17. The method of claim 16 wherein the ordered inflation/deflation steps are followed by a rest period of two to four minutes during which the ordered inflation/deflation steps are not performed.

18. The method of claim 16 wherein the ordered inflation/deflation steps are:
   a. performed at least six times,
   b. followed by a rest period during which the ordered inflation/deflation steps are not performed.

19. The method of claim 18 wherein the rest period is two to four minutes long.

20. The method of claim 15 wherein after the ordered inflation/deflation steps are repeated several times, a rest period of two to four minutes occurs before the ordered inflation/deflation steps are further repeated.

* * * * *